United States Patent
Schnell

(10) Patent No.: US 10,869,980 B2
(45) Date of Patent: Dec. 22, 2020

(54) INSERTION AID

(71) Applicant: TRACOE medical GmbH, Nieder-Olm (DE)

(72) Inventor: Ralf Schnell, Seligenstadt (DE)

(73) Assignee: TRACOE MEDICAL GMBH, Nieder-Olm (DE)

( * ) Notice: Subject to any disclaimer, the term of this patent is extended or adjusted under 35 U.S.C. 154(b) by 291 days.

(21) Appl. No.: 15/762,844

(22) PCT Filed: Dec. 19, 2016

(86) PCT No.: PCT/EP2016/081786
§ 371 (c)(1),
(2) Date: Mar. 23, 2018

(87) PCT Pub. No.: WO2017/108712
PCT Pub. Date: Jun. 29, 2017

(65) Prior Publication Data
US 2018/0280647 A1    Oct. 4, 2018

(30) Foreign Application Priority Data

Dec. 23, 2015  (DE) .......................... 10 2015 122 810

(51) Int. Cl.
*A61M 16/04* (2006.01)
*A61M 16/08* (2006.01)
(Continued)

(52) U.S. Cl.
CPC .... *A61M 16/0472* (2013.01); *A61M 16/0447* (2014.02); *A61M 16/0488* (2013.01);
(Continued)

(58) Field of Classification Search
CPC .. A61M 16/0816; A61M 25/01; A61M 29/00; A61M 25/0014; A61M 2025/0681;
(Continued)

(56) References Cited

U.S. PATENT DOCUMENTS 4,246,897 A * 1/1981 Muto ................ A61M 16/0463
128/207.15
4,502,482 A * 3/1985 DeLuccia ............. A61M 16/04
128/207.14
(Continued)

FOREIGN PATENT DOCUMENTS

DE    10 2006 029599 A1    12/2007
DE    20 2010 002803 U1    6/2010
(Continued)

OTHER PUBLICATIONS

Nora Linder, The International Bureau of the World Intellectual Property Organization, International Application PCP/EP2026/081786, English Translation of the International Preliminary Report on Patentability, dated Jul. 5, 2018.

*Primary Examiner* — Kendra D Carter
*Assistant Examiner* — Elliot S Ruddie
(74) *Attorney, Agent, or Firm* — Paul & Paul

(57) ABSTRACT

The present invention relates to a device for inserting a tracheostomy tube, comprising a guide element and a dilator, wherein the guide element has a shield, wherein, according to the invention, the guide element has a first securing means and the dilator has a corresponding second securing means, whereby the guide element can be detachably connected by positive locking to the dilator in a position in which a distal end of the dilator is engaged with an inner surface of the shield when the latter is in the first state.

12 Claims, 3 Drawing Sheets

Figure 1:
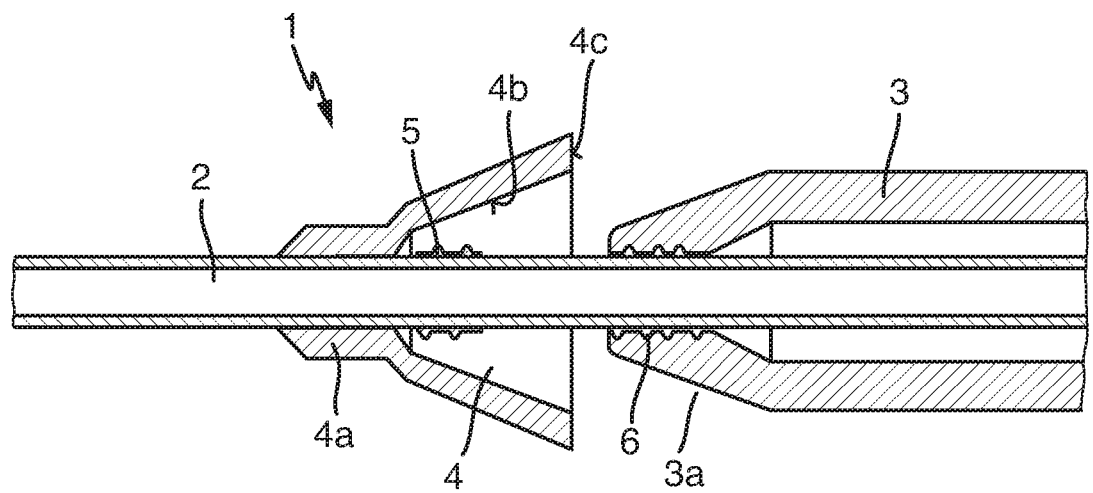

(51) Int. Cl.
*A61M 29/00* (2006.01)
*A61M 25/01* (2006.01)
*A61M 25/06* (2006.01)
*A61M 29/02* (2006.01)

(52) U.S. Cl.
CPC .... *A61M 16/0497* (2013.01); *A61M 16/0816* (2013.01); *A61M 25/01* (2013.01); *A61M 29/00* (2013.01); *A61M 29/02* (2013.01); *A61M 2025/0687* (2013.01)

(58) Field of Classification Search
CPC ...... A61M 2025/0687; A61M 25/0023; A61M 2025/0024; A61M 2025/0025; A61M 25/0026; A61M 25/0028; A61M 25/0029; A61M 25/003; A61M 2025/0031; A61M 25/0032; A61M 2039/1005; A61M 39/1011; A61M 39/16; A61M 2039/1016; A61M 2039/1022; A61M 2039/1027; A61M 2039/1033; A61M 2039/1038; A61M 2039/1044; A61M 39/105; A61M 9/1055; A61M 2039/1061; A61M 2039/1066; A61M 2039/1072; A61M 2039/1077; A61M 2039/1083; A61M 2039/1088; A61M 2039/1094; A61M 39/12; A61M 39/14; A61M 16/0465–16/0497; A61M 29/02; A61M 2029/025; A61M 25/0034; A61M 16/0463–0465; A61M 39/02; A61M 39/10
See application file for complete search history.

(56) References Cited

U.S. PATENT DOCUMENTS

| | | |
|---|---|---|
| 5,827,324 A | 10/1998 | Cassell et al. |
| 6,481,436 B1 | 11/2002 | Neame |
| 2004/0154623 A1 | 8/2004 | Schaeffer et al. |
| 2009/0178674 A1* | 7/2009 | Schnell ............. A61B 17/3415 128/200.26 |
| 2011/0041854 A1* | 2/2011 | Rasor ................ A61B 17/3415 128/207.15 |

FOREIGN PATENT DOCUMENTS

| | | | |
|---|---|---|---|
| EP | 1044701 A2 | 10/2000 | |
| WO | 2006087512 A1 | 2/2005 | |
| WO | 2015/078114 A1 | 11/2013 | |
| WO | WO-2015078114 A1 * | 6/2015 | ........ A61M 16/0472 |

* cited by examiner

INSERTION AID

CROSS-REFERENCE TO RELATED APPLICATIONS

This is a national stage 371 application of International Application No. PCT/EP2016/081786, filed Dec. 19, 2016, which claims the priority of German Patent Application 10 2015 122 810.6, filed Dec. 23, 2015, each of which is incorporated herein in its entirety.

The present invention relates to a device for inserting a tracheostomy tube, comprising a guide element and a dilator, wherein the dilator is tubular and the guide element can be introduced into the dilator at least in sections, wherein the guide element has a shield, which has a conical shape, with a tip and a shield wall and a base, wherein the guide element passes through the axis of the shield and the tip, and the shield in the area of the tip is securely connected to the guide element and wherein the shield has a first and a second state and wherein the shield in the first state has a conical shape and in the second state is deformed compared with this conical shape, as well as a tracheostomy tube with such an insertion aid.

Devices of the above-named type which are suitable for the insertion of a tracheostomy tube, in particular into a tracheostoma that is yet to be widened, are known to a person skilled in the art. DE 10 2006 029 599 describes such an insertion aid in which a shield is attached to a guide element, which shield, in the introduced state, can cover a dilator running in the tracheostomy tube in the area of its tip, which protrudes from the tracheostomy tube at a distal end thereof, and bridges over a stepped sudden change in calibre at the transition between the dilator protruding from the distal end of the tube and the outside diameter of the tube at its distal end.

In particular in the case of tubes with a large wall thickness at the distal tube end, such an abrupt transition can represent a problem when it comes to the widening of a tracheostoma, if the distal end of the tube jams for example against a tracheal ring and thus causes a cartilage fracture or, as a result of the increased exertion of force to introduce the tracheostomy tube, hits the rear wall of the trachea and causes an injury to the latter.

The device shown in DE 10 2006 029 599 in principle allows a safer introduction of a tracheostomy tube into a tracheostoma to be widened. However, the device requires very precise handling, during which great care must be taken to ensure that the shield with guide element applied to the dilator is fixed or held tight when the tube is inserted in order to prevent the guide element with shield from being pushed in the direction of the proximal end of the tracheostomy tube by the force acting on the shield tip when the tracheostoma is widened. If this care is not taken or, in individual cases, if the tracheostomy tube is withdrawn carelessly during the insertion phase, there is the risk that the silicone shield on the guide element will become detached from the tip of the dilator and thus no longer cover the distal end of the tracheostomy tube. The device shown in DE 10 2006 029 599 can thus no longer exert its advantageous effect and this ultimately leads to a much more difficult insertion of the tracheostomy tube into the trachea as an atraumatic transition between dilator and tracheostomy tube is no longer guaranteed. This leads to the above-described problems that occur when a sudden change in calibre is not covered.

OBJECT

Against the background of this state of the art, the object of the present invention is to prevent an unintentional detachment of a shield covering a sudden change in calibre in the case of an insertion aid for a tracheostomy tube.

According to the invention this object is achieved by a device of the type named at the beginning, wherein the guide element has a first securing means and the dilator has a corresponding second securing means, whereby the guide element can be detachably connected by positive locking to the dilator in a position in which a distal end of the dilator is engaged with an inner surface of the shield when the latter is in the first state.

Such an embodiment allows a separate introduction of the guide element with shield from the distal end into the tracheostomy tube to be inserted and of the dilator from the proximal end into the tracheostomy tube to be inserted and a subsequent positive-locking connection of the guide element to the dilator in a position in which the shield on the guide element in its first state is engaged with an inner surface with the distal end of the dilator and thus covers the distal end thereof. The shield is thus capable of performing its function as part of the device and covering the sudden change in calibre between dilator and tracheostomy tube which is to be inserted, wherein at the same time an unintentional detachment is prevented.

Before use of the device according to the invention, the guide element with shield is pushed from the distal end into the tracheostomy tube to be inserted and the dilator is pushed from the proximal end into the tracheostomy tube to be inserted and dilator and guide element are then connected to each other with the aid of the first and second securing means. In addition, the shield is then brought into its first state, in which the dilator is engaged with the inner surface of the shield. The device according to the invention is thus assembled inside a tracheostomy tube to be inserted.

In particular, this also allows the use of the device according to the invention for very narrow and/or strongly curved tracheostomy tubes, into which such an insertion device would otherwise not be able to be inserted.

When the dilator is inserted into a tracheostomy tube, the distal end of the dilator protrudes distally beyond the distal opening of the tracheostomy tube. The shape of the protruding area is preferably substantially conical. Correspondingly the shape of the inner surface of the shield is also substantially conical. By virtue of such a shape, a particularly good force transmission from the dilator to the shield takes place, with the result that by means of the combination of such a dilator and shield a widening of the tracheostoma and insertion of the tracheostomy tube are facilitated.

In the case of percutaneous dilatational tracheostomy, for which the device is provided, instead of the proposed tracheostoma, a guide wire, also called a Seldinger guide wire, is first introduced into the trachea with the aid of a puncture needle. By means of the guide wire, a dilator with an outside diameter of 14 French (14 French dilator) is guided and the existing puncture channel is widened, with the result that a guide catheter can then be introduced into the trachea by means of the guide wire. When the device according to the invention is used, this is the guide element. With the aid of the guide element of the device and with the dilator of the device, as it is described here, a dilation of the puncture channel is then effected by careful insertion of the device into the puncture channel, wherein the guide wire acts as a type of guide rail. The device, which is introduced into a tracheostomy tube and in which the shield covers the sudden change in calibre between dilator and distal end of the tracheostomy tube, is thus pushed into the widened puncture channel for the widening and ultimately insertion of the tracheostomy tube. The dilator is then withdrawn from the tracheostomy tube together with the guide element with shield connected thereto in the proximal direction. With the aid of a single device, therefore, a puncture channel is widened to form a tracheostoma, into which the tracheostomy tube is simultaneously inserted.

The device according to the invention can be used in the same way to change tubes, wherein no new puncture is necessary through the already existing tracheostoma, which contracts partially but not completely when the tracheostomy tube is removed.

Unlike in the case of the conventional tracheostomy tube according to Ciaglia, in the case of the device according to the invention it is not strictly necessary first to widen the tracheostoma with one or more separate dilators, which are then withdrawn again, in order to subsequently introduce the tracheostomy tube, optionally with a device for insertion into the already widened tracheostoma.

Nevertheless, the device according to the invention can of course—as described above—also be used to introduce a tracheostomy tube into an already widened tracheostoma.

In the case of the insertion aid according to the invention, it is further provided that, after introduction of the tracheostomy tube into the tracheostoma, the device located in the tracheostomy tube is withdrawn from the tracheostomy tube with the aid of the dilator in the direction of the proximal end. By virtue of the detachable connection of the guide element to the dilator in the connected state, both guide element and shield together with the dilator are withdrawn from the tracheostomy tube in the direction of the proximal end. For this withdrawal, the shield transitions from its first state into its second state. During the transition of the shield from the first into the second state, the inner surface of the shield and the distal end of the dilator are at least partially disengaged and the shield deforms in such a way that its outside diameter at every point is smaller than or equal to the inside diameter of the tracheostomy tube, which is introduced with the device.

A positive-locking connection provides a particularly good safeguard against an unintentional detachment. However, this does not rule out the possibility of there being, in addition to the positive-locking connection, also a frictional connection between the two securing means or a further detachable connection between guide element and/or shield on the one hand and the dilator on the other hand.

The dilator is preferably not engaged with the inner surface of the shield when it is in its second state. In an embodiment, the shield in its second state is at least partially or completely inverted in comparison with the first state. The shield in its second state is deformed such that its outside diameter at every point is smaller than or equal to the inside diameter of the tracheostomy tube, which is to be introduced with the device.

The terms "distal" and "proximal" as used here are based on the point of view of the persons inserting the tracheostomy tube with the device, i.e. the "distal" end denotes the end or the area which is inserted into the patient and the "proximal" end denotes the end or the area which points outwards away from the patient. During insertion of the insertion aid, a distal end of the guide element is thus first inserted into the patient through the tracheostoma to be widened, wherein this is preferably effected by means of a guide wire which then runs inside the tubular guide element.

The "guide element" denotes a tubular article within the meaning of the invention. The lumen of the tubular guide element preferably has an inside diameter which is larger than the outside diameter of a Seldinger guide wire provided for a tracheostomy, preferably larger than 1.3 mm. In an embodiment, the outside diameter of the Seldinger guide wire is from 1 mm to 1.3 mm, wherein the inside diameter of the guide element is preferably between 0.1 and 0.5 mm larger than the outside diameter of the Seldinger guide wire.

The outside diameter of the "guide element", at least in a proximal section of the guide element, is smaller than the inside diameter of the dilator of the device for inserting a tracheostomy tube and is preferably from 2.7 mm to 4 mm.

In an embodiment, the guide element is a guide catheter, i.e. a hose-like element with substantially constant inside and outside diameter. In an embodiment, the outside diameter of the guide element is larger or smaller in various sections than in other sections, the outside diameter is preferably smaller in the area in which the tip of the shield is connected to the guide element than in the other areas.

In an embodiment, the outside diameter of the distal end of the guide catheter preferably narrows.

The "dilator" denotes an element which is tubular at least at its distal end and in an adjoining section, with an outside diameter which is smaller than the inside diameter of a tracheostomy tube to be inserted with the device. The dilator further has a shaft, which also has an outside diameter which is smaller than the inside diameter of the tracheostomy tube to be inserted, and a grip, wherein the grip at least in a section has an outside diameter which is larger than the inside diameter of the tracheostomy tube, with the result that the grip cannot be inserted into the tracheostomy tube. At least the distal end and the adjoining section have a lumen with an inside diameter which is larger than or equal to the outside diameter of the guide element; the inside diameter is preferably from 2.7 mm to 4 mm. The guide element can thereby be inserted into the dilator, at least in this area. The outside diameter of the dilator, at least in the section adjoining the distal end, is preferably from 0.2 mm to 4 mm, preferably from 1 mm to 1.5 mm, smaller than the inside diameter of the tracheostomy tube to be inserted with the device. The section adjoining the distal end preferably has an axial length of from 2 mm to 4 cm, preferably 5 mm to 2 cm.

In an embodiment, the dilator has the shape of a conventional dilator, i.e. it is a completely tubular element which is curved at least in sections, with a preferably conical distal end and a proximal grip area, wherein the grip area at least in a section has an outside diameter which is larger than the inside diameter of the tracheostomy tube to be inserted with the device. Such an embodiment is suitable for use with a guide element which is designed as a guide catheter, wherein the guide catheter is longer than the axial length of a tracheostomy tube to be inserted with the device.

In an embodiment, a flexible rod-shaped or tubular area adjoins the section adjoining the distal end as a shaft, the outside diameter of which is less than half the inside diameter of the tracheostomy tube to be inserted with the device. In the case of an embodiment with a rod-shaped shaft, a Seldinger guide wire to be guided through the dilator during the introduction runs not through the shaft of the dilator but along the shaft, contrary to other embodiments with a completely tubular dilator.

The shield is located on the guide element, preferably closer to the distal end of the guide element than to the proximal end of the guide element, and its tip points in the direction of the distal end of the guide element.

The wording "the guide element has a first securing means [ . . . ]", as used herein, includes that the first securing means is located directly on the guide element or on the shield connected to the guide element.

The term "conical shape" as used here refers to the fact that the shield, essentially consisting of a tip and a shield wall, at least in its first position has a shield wall with an outside diameter that increases from the tip to the base without abrupt widening, wherein the contour of the cone can also have a concave or convex curvature. The shield wall has an outer surface and the inner surface of the shield, wherein the conical shape is substantially formed by the outer surface of the shield wall. The shield wall, at least in the first state, preferably substantially has the shape of a hollow cone.

The term "base" of the shield denotes the plane of the shield, in particular of the shield wall, perpendicular to its axis which has the greatest diameter.

The distal end of the tip of the shield is preferably located at a distance of from 1 mm to 8 cm, preferably 3 mm to 5 cm, from the distal end of the guide element. In another embodiment, the tip of the shield is located at the distal end of the guide element and the latter does not protrude distally beyond the tip of the shield.

The axial length of the shield is preferably between 1 cm and 7 cm, particularly preferably between 1.5 cm and 4 cm.

It is also preferred for the cone angle between the shield and the longitudinal axis of the guide element to be between 2° and 20°, preferably between 5° and 11°. It is preferred if the shield in the first state substantially has the shape of a hollow cone and is internally and externally conically shaped.

It is likewise preferred for the shield to be developed such that it is partially or completely inverted in order to go from the first into the second state.

In an embodiment, the base of the shield has a hollow cylinder-shaped attachment, with an outside diameter which is matched to the inside diameter of a tracheostomy tube to be inserted and is larger than or smaller than same by a maximum of 10%, preferably a maximum of 5%, relative to the inside diameter of the tracheostomy tube to be inserted, and with a wall thickness which is between 0.5 mm and 2 mm, preferably between 0.5 mm and 1 mm. It is advantageous if the shield has a maximum wall thickness at the base of at most 2.5 mm, preferably at most 1.8 mm and at least 0.4 mm, preferably at least 0.5 mm.

In an embodiment, the shield consists of or comprises silicone or thermoplastic elastomers, including thermoplastic elastomers based on olefin (TPO), thermoplastic elastomers based on urethane (TPU), thermoplastic polyester elastomers (TPC), including copolyester, styrene block copolymers (TPS), including SBS, SEBS, SEPS, SEEPS and MBS, or thermoplastic copolyamides (TPA).

At its base, the shield in the first state preferably has an outside diameter which is larger than the inside diameter of the tracheostomy tube to be inserted with the device at its distal end, and preferably corresponds to the outside diameter of a tracheostomy tube to be inserted with the device at its distal end, and in its second state has a smaller outside diameter than the inside diameter of the tracheostomy tube due to deformation, with the result that it can be pulled through the latter. The deformation of the shield during the transition between first and second state is preferably effected by complete or partial inversion, in particular when the dilator is withdrawn from the tracheostomy tube. The wording "corresponds to the outside diameter of a tracheostomy tube to be inserted with the device at its distal end" in relation to the outside diameter of the base of the shield within the meaning of the invention also includes shields with an outside diameter at the base which is up to 0.5 mm larger or smaller than the outside diameter of the tracheostomy tube at its distal end owing to tolerance deviations.

Similarly, the dilator has an outside diameter which is smaller than the inside diameter of the tracheostomy tube to be inserted with the device. The tubular dilator further preferably has an inside diameter which, at least in a distal section of the dilator, is larger than the outside diameter of the guide element and is preferably smaller than the respectively largest outside diameter of the shield in the first and/or second state, with the result that the guide element with shield cannot be guided through the dilator.

It is understood that the outer contour of the dilator, preferably at least in a section, substantially has the inner contour of the tracheostomy tube to be inserted with the device and in particular the curvature thereof. The dilator preferably has a grip at its proximal end.

It is also preferred that the second securing means is located on the dilator at the distal end and the first securing means is located on the guide element in an area which, in the unconnected state of the securing means, in the first state of the shield is covered by the shield and in the second state of the shield is at least partially visible.

Such an arrangement makes it possible, after the dilator has been introduced into the tracheostomy tube, wherein this introduction is preferably effected from the proximal end, to pass the guide element through the dilator from the distal direction until the shield is located in the area of the distal, first end of the dilator. By manually transferring the shield into the second state it is thus possible to connect the first securing means to the second securing means and then to transfer the shield back into the first state, with the result that both securing means are covered by the shield at least as far as possible.

In an embodiment, the first securing means is located on the outside of the guide element or a sleeve arranged around the guide element, which lies against the outer wall thereof and can be part of the shield.

In an embodiment, the first securing means and the second securing means form a turn-lock fastener, preferably a threaded fastener or a bayonet fastener. The common feature of these fasteners is that the connection is formed and released by a rotary movement.

In an embodiment, in the case of the threaded fastener an external thread is located on the outer circumference of the guide element and an internal thread is located on the inner circumference of the tubular dilator.

In an embodiment, in the case of a bayonet fastener a lug is located on the outer circumference of the guide element, while the recess necessary for locking the bayonet fastener in place is located on the inner circumference of the tubular dilator.

In an embodiment, the first securing means is formed in one piece with the guide element and/or the second securing means is formed in one piece with the dilator.

In an embodiment, the first securing means and the second securing means form a detent connection. In the case of such a detent connection, the first securing means or the second securing means has at least one detent which preferably catches with elastic pretension in a corresponding recess on the respectively other securing means.

In certain embodiments, combinations of different releasable connections between guide element and/or shield on the one hand and the dilator on the other hand are also conceivable and within the meaning of the invention.

In an embodiment, the silicone shield has a grooved structure on its inner surface and the dilator has a corresponding grooved structure at the distal end, wherein the grooves of the grooved structure preferably extend in the longitudinal direction. The grooved structure forms a further safeguard against an unintentional detachment of the shield from the dilator.

In an embodiment, a grooved structure extending in the longitudinal direction is combined with a turn-lock fastener. In the case of such a combination, the grooved structure additionally prevents a loosening of the rotary connection due to the dilator and shield twisting against each other, as it forms a positive-locking connection with regard to the rotary movement.

In an embodiment, the shield with its inner surface lies against the distal end of the dilator in the connected state of the securing means and in the first state of the shield with an elastic pretension. This represents a further safeguarding function of the fastening which additionally prevents an unintentional release for example of a connection made by positive locking by means of a frictional connection.

The above-named object is also achieved by a tracheostomy tube with an above-described insertion aid.

In an embodiment, the dilator in the area of its proximal end has a third securing means, with which the dilator can be detachably connected to the proximal end of the cannula tube and/or to a fourth securing means at the proximal end of the cannula tube. With the aid of this third securing means, with which in addition to the fixing of the guide element on the dilator the dilator is also detachably secured to the tracheostomy tube, the dilator is prevented from shifting in the longitudinal direction in the tracheostomy tube during the insertion of the tracheostomy tube. By means of such a design an additional source of errors is ruled out and the handling is further simplified for the person inserting the tracheostomy tube.

In an embodiment, the fourth securing means is located directly on the cannula tube of the tracheostomy tube.

The third securing means preferably comprises a union nut and/or a clamp and/or a connector. It is understood that in the case of a union nut the proximal end of the cannula tube must have a corresponding thread in order to ensure a fastening.

A connector is used in particular in the case of tracheostomy tubes in which a connector is provided as fourth securing means for the fastening of a breathing tube at the proximal end of the cannula tube. In the case of such a frictional connection the third securing element is designed such that it lies externally against the substantially conical connector narrowing in the direction of the proximal end and corresponds to the shape thereof.

Figure 2:
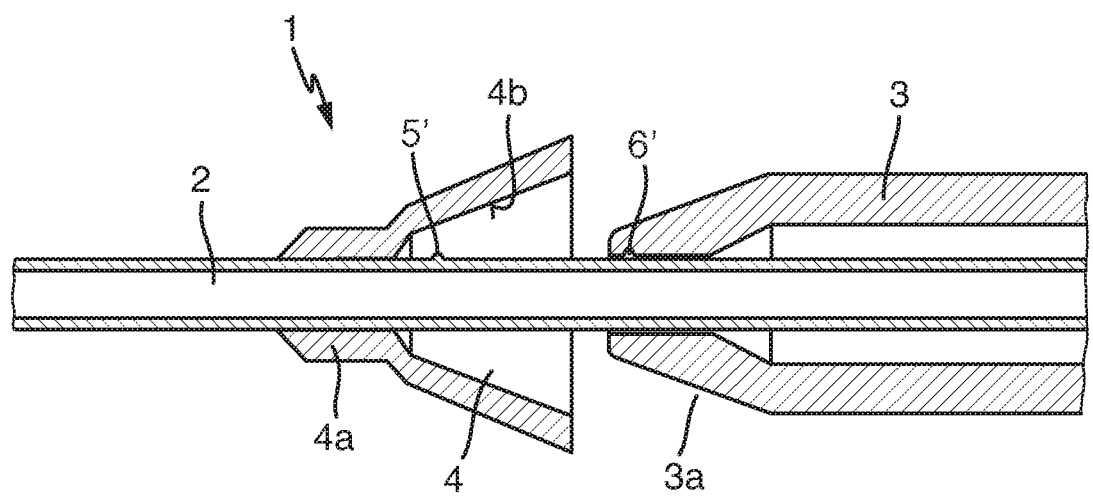
Figure 3:
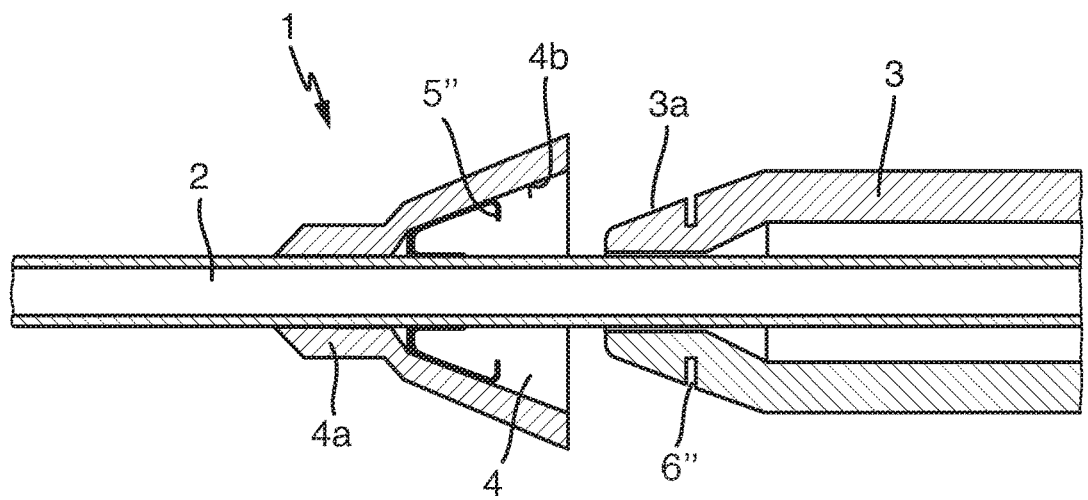
Figure 4:
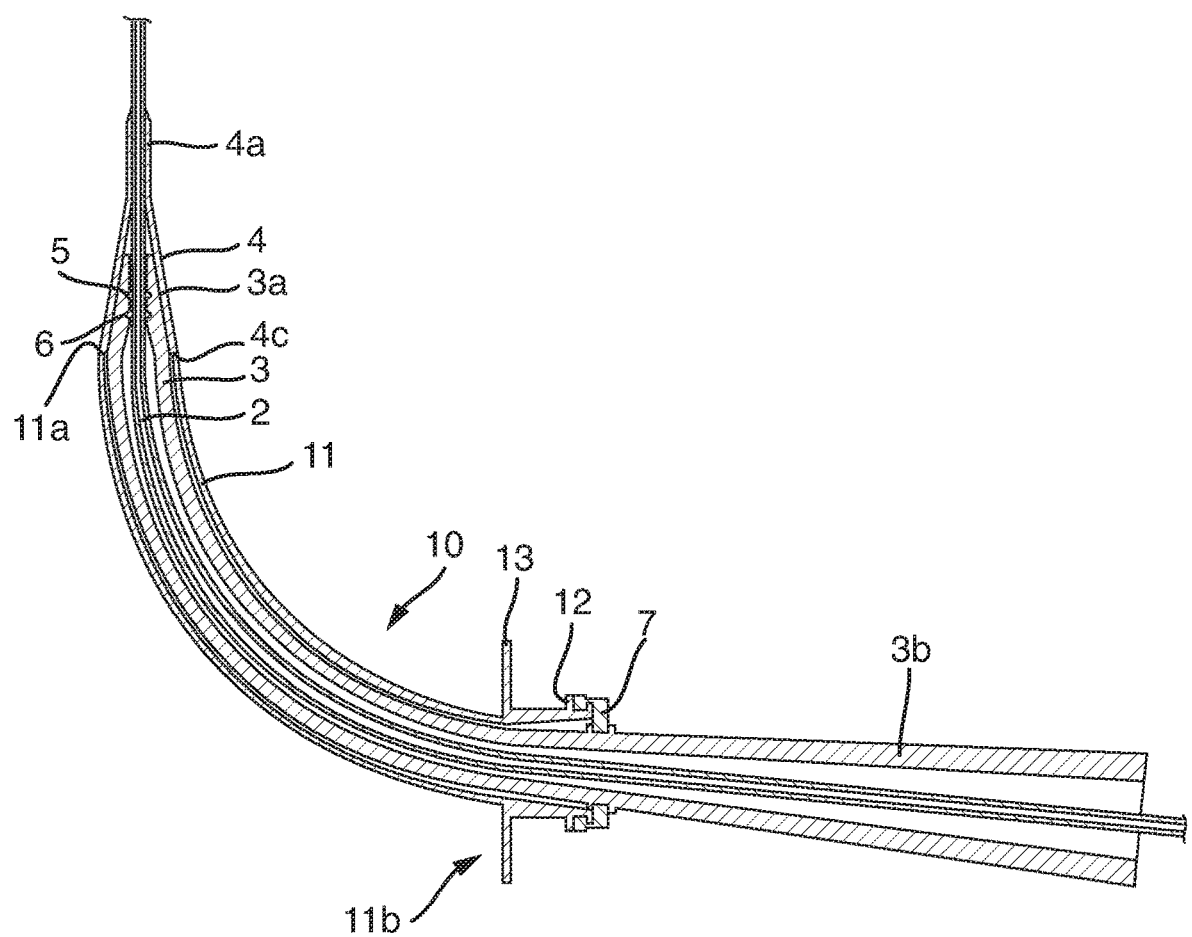
Figure 5:
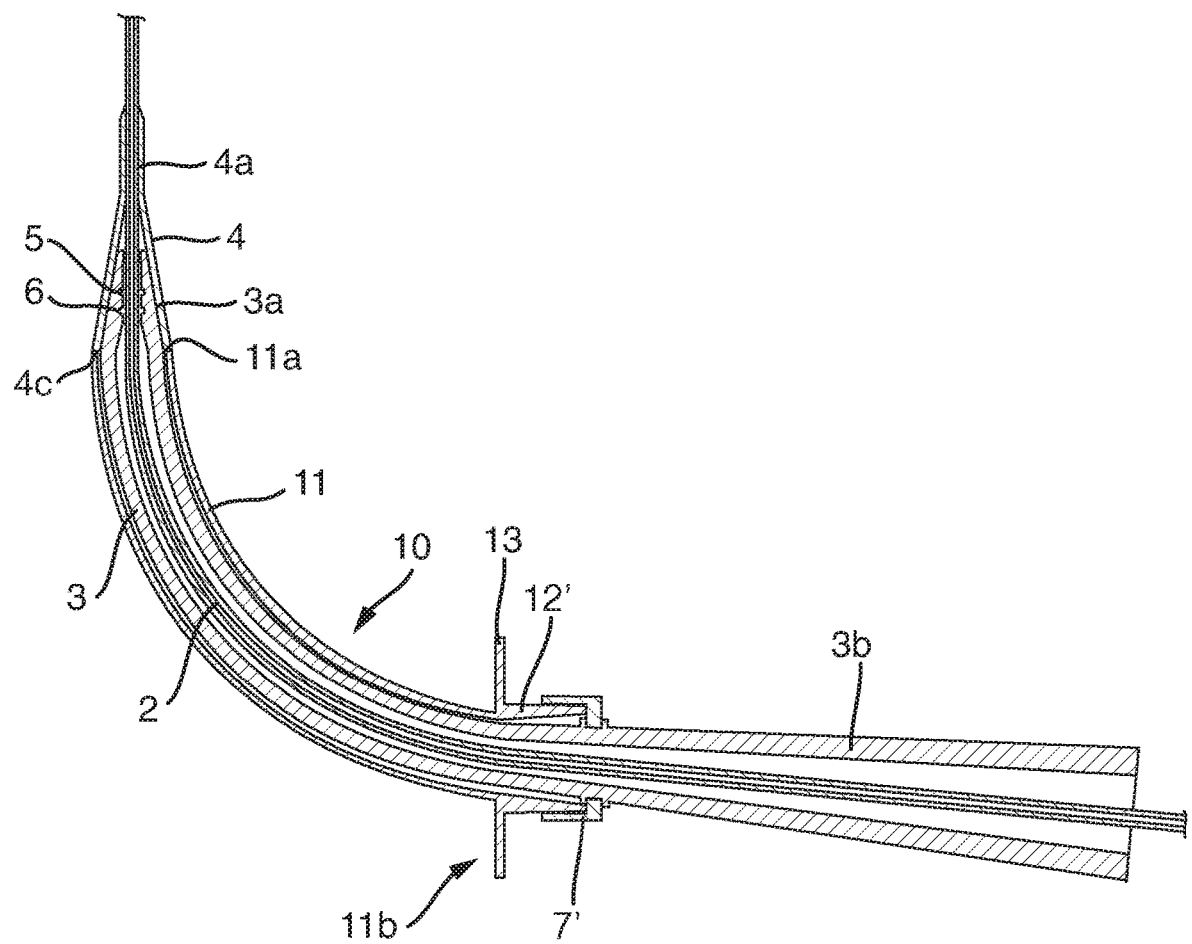

Further advantages, features and possible applications of the present invention become clear with reference to the following descriptions of preferred embodiments and the associated figures. It is understood that the figures are merely schematic representations and are in no way to be understood as true-to-scale or conformal reproductions. Regardless of the hatching used, the elements of the embodiments represented in the figures preferably consist of plastic. There are shown in:

FIG. 1: a detail of a longitudinal section of an embodiment of an insertion aid according to the invention, FIG. 2: a detail of a longitudinal section of a further embodiment of an insertion aid according to the invention, FIG. 3: a detail of a longitudinal section of a further embodiment of an insertion aid according to the invention, FIG. 4: a longitudinal section through an insertion aid according to the invention which in the connected state is located inside a tracheostomy tube, and FIG. 5: a longitudinal section through a further insertion aid according to the invention which in the connected state is located inside a tracheostomy tube.

Represented in cross section in FIG. 1 is a device 1 according to the invention for inserting a tracheostomy tube, which comprises a guide element 2 as well as a dilator 3. A shield 4, which in the area of its tip 4a is securely connected to the guide element, is located on the guide element 2. A first securing means 5, which in this embodiment is an external thread, is further located on the guide element. In the first state of the shield represented in FIG. 1, the first securing means in this embodiment is located in an area which is completely covered by the shield. A second securing means 6, which in this embodiment is an internal thread, and corresponds to the first securing means 5 on the guide element 2, is located at the distal end 3a of the dilator 3.

The tubular dilator further has a lumen the cross section of which at every point is at least slightly larger than the outside diameter of the guide element, with the result that the guide element, with all areas in which no securing means or shield is located, can be pushed into the dilator.

It is also clearly recognizable from FIG. 1 that, in the connected state of the first and second securing means, the distal end 3a of the dilator is engaged with the inner surface 4b of the shield, provided the shield, as shown in FIG. 1, is in its first state. The conical shape of the shield is thus supported by the dilator in the connected state and in the first state of the shield and the dilator provides the shield with the necessary stability for widening a tracheostoma.

The embodiment shown in FIG. 2 substantially corresponds to the one shown in FIG. 1. The insertion aid 1 has a guide element 2 and a dilator 3. A shield 4, wherein the shield with its tip 4a is securely connected to the guide element 2, is located on the guide element 2. Further, a first securing means 5' is located on the guide element 2 and a second securing means 6' is located on the dilator 3, wherein the second securing means in this embodiment is also substantially located in the distal area of the dilator 3.

In this embodiment, a bayonet fastener is formed by the first and second securing means 5', 6', wherein a fastening by positive locking also comes about by performing a rotary movement, as in the case of the turn-lock fastener shown in FIG. 1.

In this embodiment, the distal end 3a of the dilator 3 also substantially corresponds to the inner surface 4b of the shield 4, with the result that, in a position in which the guide element is connected to the dilator if the shield is in the first state, the distal end 3a of the dilator 3 is engaged with the inner surface 4b of the shield 4.

FIG. 3 also shows an embodiment according to the invention of a device 1 for inserting a tracheostomy tube, which comprises a guide element 2 and a dilator 3. A shield 4, which with its tip 4a is securely connected to the guide element 2, is located on the guide element 2. The guide element further has a first securing means 5", which constitutes two pretensioned clamps, and the dilator has a second securing means 6", which constitutes two recesses with which the clamps in the connected state are engaged. The clamps of the first securing means 5" are pretensioned such that a release of the connection to the second securing means 6" is only possible by overcoming the pretension.

In this embodiment, the distal end of the dilator 3a also substantially corresponds to the inner surface of the shield 4b, with the result that, in the connected state, when the shield is in its first state, the distal end of the dilator is engaged with the inner surface of the shield.

A tracheostomy tube 10 with a device 1 according to the invention is represented in FIG. 4, wherein the device 1 substantially corresponds to the embodiment shown in FIG. 1, which means that the first securing means 5 and the second securing means 6 form a rotary connection, wherein the first securing means is an external thread attached to the outside of the guide element 2 and the second securing means is an internal thread located in the lumen of the dilator. In the connected state, both the first securing means 5 and the second securing means 6 and also the distal end 3a of the dilator 3 are covered by the shield, which is located on the guide element 2. The distal end of the dilator 3a engages with the inner surface 4b of the shield 4, which is in its first state. The guide element 2 in this embodiment is designed as a guide catheter.

The tracheostomy tube 10 has a cannula tube 11, wherein in FIG. 4 it is clearly recognizable that the base 4c of the shield 4 covers the distal end 11a of the cannula tube, wherein the base 4c of the shield 4 has an outside diameter which substantially corresponds to or is slightly larger than the outside diameter of the cannula tube 11. By means of this design, the sudden change in calibre between the distal end 3a of the dilator 3 and the distal end of the cannula tube 11a is completely covered by the shield.

In the embodiment shown in FIG. 4, a fourth securing means 12, which is connected to a third securing means 7 on the dilator 3 in the position shown in FIG. 4, is further located at the proximal end 11b of the cannula tube 11. The third securing means 7 in this embodiment is a union nut which engages in a corresponding recess or a thread of the fourth securing means 12. The grip of the dilator 3b is additionally designed such that it cannot be pushed into the cannula tube 11 of the tracheostomy tube 10 even independently of the third securing means 7, as its outside diameter is larger than the inside diameter of the tracheostomy tube 10.

A neck flange 13 is indicated merely schematically on the tracheostomy tube 10, with which, with the aid of a neck strap, the tracheostomy tube can be fastened to a patient's neck. The precise design of the neck flange, however, is irrelevant for the present invention; it is therefore indicated rudimentarily only for the sake of completeness.

A tracheostomy tube 10 with a device 1 according to the invention is likewise represented in FIG. 5. The embodiment shown in FIG. 5 substantially corresponds to the one shown in FIG. 4; therefore reference is made to the specifications there.

However, the embodiment in FIG. 5 differs from the one shown in FIG. 4 by the type of the third securing means 7' and fourth securing means 12'. The fastenings shown in FIG. 5 constitute a frictional connection. The fourth securing means 12' narrows at the proximal end 11b of the cannula tube 11 in the proximal direction and has the shape of a usual 15-mm connector. The third securing means 7' on the dilator 3 has an inner surface corresponding to the outer surface of the fourth securing means 12', wherein the third securing means 7' in the connected state is frictionally connected to the outer surface of the fourth securing means 12'.

LIST OF REFERENCE NUMBERS 1 device for inserting a tracheostomy tube
2 guide element
3 dilator
3a distal end of the dilator
3b grip of the dilator
4 shield
4a tip of the shield
4b inner surface of the shield
4c base of the shield
5, 5', 5" first securing means
6, 6', 6" second securing means
7, 7' third securing means
10 tracheostomy tube
11 cannula tube
11a distal end of the cannula tube
11b proximal end of the cannula tube
12, 12' fourth securing means
13 neck flange

The invention claimed is:

1. Device for inserting a tracheostomy tube, comprising a guide element and a dilator, wherein the dilator is tubular and the guide element can be introduced into the dilator at least in sections, wherein the guide element is directly in contact with a shield, said shield having a tip and a shield wall and a base, wherein the guide element passes along an axis of the shield and of the tip of the shield, and the shield in the area of the tip is securely connected to the guide element and wherein the shield has a first and a second state and wherein the shield in the first state has a conical shape and in the second state is deformed compared with this conical shape, characterized in that the guide element has a first securing means and the dilator has a corresponding second securing means, whereby the guide element can be detachably connected by positive locking to the dilator in a position in which a distal end of the dilator is engaged with an inner surface of the shield when the shield is in the first state.

2. Device according to claim 1, characterized in that, at the base of the shield, the shield in the first state has an outside diameter which is larger than the inside diameter at a distal end of the tracheostomy tube to be inserted with the device, and wherein the shield in the second state of the shield has a smaller outside diameter than the inside diameter of the tracheostomy tube to be inserted with the device due to deformation.

3. Device according to claim 2, characterized in that, at the base of the shield, the shield in the first state has an outside diameter that corresponds to the outside diameter at the distal end of the tracheostomy tube to be inserted with the device.

4. Device according to claim 1, characterized in that the second securing means is located on the dilator at the distal end and the first securing means is located on the guide element in an area which, in an unconnected state of the first and second securing means, in the first state of the shield is completely covered by the shield and in the second state of the shield is not completely covered by the shield.

5. Device according to claim 1, characterized in that the first securing means and the second securing means form a turn-lock fastener.

6. Device according to claim 5, characterized in that the first securing means and the second securing means form a threaded fastener or a bayonet fastener.

7. Device according to claim 1, characterized in that the first securing means and the second securing means form a detent connection.

8. Device according to claim 1, characterized in that the inner surface of the shield has a grooved structure and the dilator has a corresponding grooved structure at the distal end, wherein the grooves of the grooved structure extend in the longitudinal direction.

9. Device according to claim 1, characterized in that the inner surface of the shield lies against against the distal end of the dilator in a connected state of the first and second securing means, and in the first state of the shield with an elastic pretension.

10. Tracheostomy tube, having a cannula tube with a proximal end and a distal end, with a device according to claim 1.

11. Tracheostomy tube according to claim 10, characterized in that the dilator in the area of the proximal end of the dilator has a third securing means, with which the dilator can be detachably connected to the proximal end of the cannula tube or to a fourth securing means at the proximal end of the cannula tube.

12. Tracheostomy tube according to claim 11, characterized in that the third securing means comprises a union nut or a clamp or a connector.

* * * * *

UNITED STATES PATENT AND TRADEMARK OFFICE
CERTIFICATE OF CORRECTION

PATENT NO. : 10,869,980 B2
APPLICATION NO. : 15/762844
DATED : December 22, 2020
INVENTOR(S) : Ralf Schnell Page 1 of 1

It is certified that error appears in the above-identified patent and that said Letters Patent is hereby corrected as shown below:

In the Claims

Column 10, Line 67, Claim 9, delete second occurrence of "against"

Column 11, Line 13, Claim 12, change "claim 11" to -- claim 10 --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*